United States Patent [19]

Hildebrand et al.

[11] 4,258,574
[45] Mar. 31, 1981

[54] METHOD AND APPARATUS FOR ULTRASONIC IMAGING USING A LINE SOURCE AND A LINEAR RECEIVER ARRAY

[75] Inventors: B. Percy Hildebrand; S. R. Doctor, both of Richland, Wash.

[73] Assignee: Electric Power Research Institute, Palo Alto, Calif.

[21] Appl. No.: 20,979

[22] Filed: Mar. 16, 1979

[51] Int. Cl.³ ............................................. G01N 29/04
[52] U.S. Cl. .................................................... 73/625
[58] Field of Search ................. 73/606, 607, 618, 620, 73/624, 625, 626, 627, 628, 632, 633, 641; 367/103, 104, 105, 125

[56] References Cited

U.S. PATENT DOCUMENTS

| | | | |
|---|---|---|---|
| 3,953,825 | 4/1976 | Kino et al. | 73/626 |
| 4,174,635 | 11/1979 | Oldendorf | 73/606 |

FOREIGN PATENT DOCUMENTS 772083  4/1957  United Kingdom ...................... 73/626

OTHER PUBLICATIONS

A. L. Boyer et al., "Computer Reconstruction of Images From Ultrasonic Holograms,"*Acoustical Holography*, vol. 2, pp. 211-223, Mar. 1969.
David Lee Van Rooy, "Digital Ultrasonic Wavefront Reconstruction in the Near Field," IBM Publication No. 320.2402, pp. 1-81, May 19, 1971.
G. Wade et al., "A Holographic System for Use in the Ocean," *Acoustical Holography*, vol. 3, pp. 225-245, 1971.
M. Wollman et al., "Experimental Results From an Underwater Acoustical Holographic System," *Acoustical Holography*, vol. 5, pp. 159-174, 1974.
A. L. Boyer et al., "Computer Reconstruction of Images From Ultrasonic Holograms," IBM Publication No. 320.2363, pp. 1-17, Mar. 7, 1969.

*Primary Examiner*—Stephen A. Kreitman
*Attorney, Agent, or Firm*—Flehr, Hohbach, Test

[57] ABSTRACT

Method and apparatus for ultrasonically imaging objects of interest. The apparatus includes an elongate source of coherent acoustic waves which are brought to a line focus and propagated in an object of interest. The acoustic waves are detected by an elongate linear array of substantially point receivers which are located parallel to the elongate source and substantially at the line focus. The elongate source and the linear receiver array are translated together relative to the object of interest so that an area is swept out across the object of interest. The amplitude and the phase of the acoustic waves scattered by the object of interest are detected by the receiver array, digitized and back wave reconstructed to yield a digital image of the object of interest.

14 Claims, 4 Drawing Figures

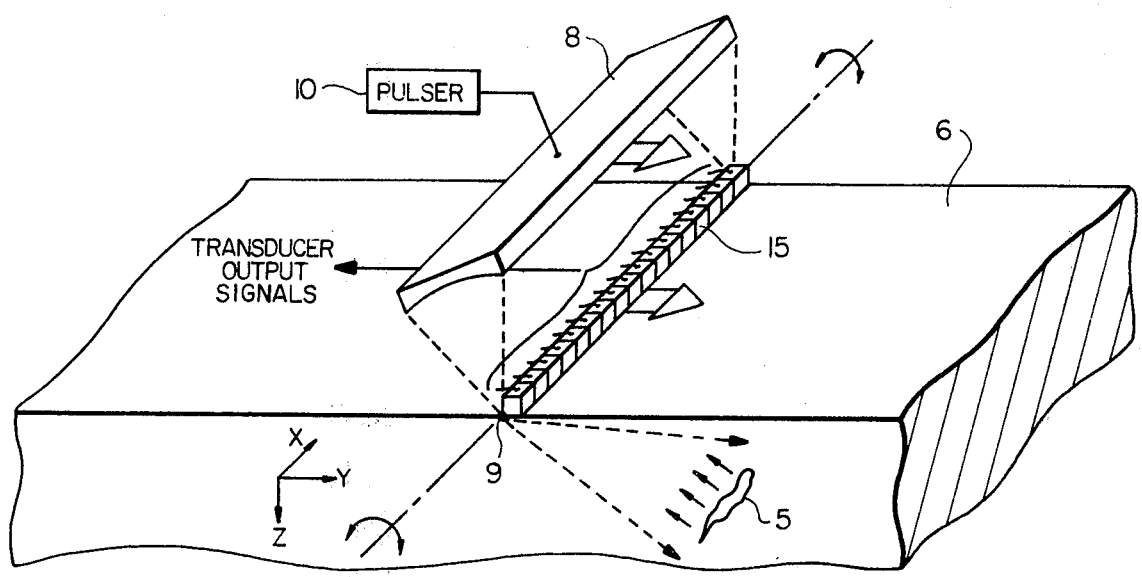
FIG__1
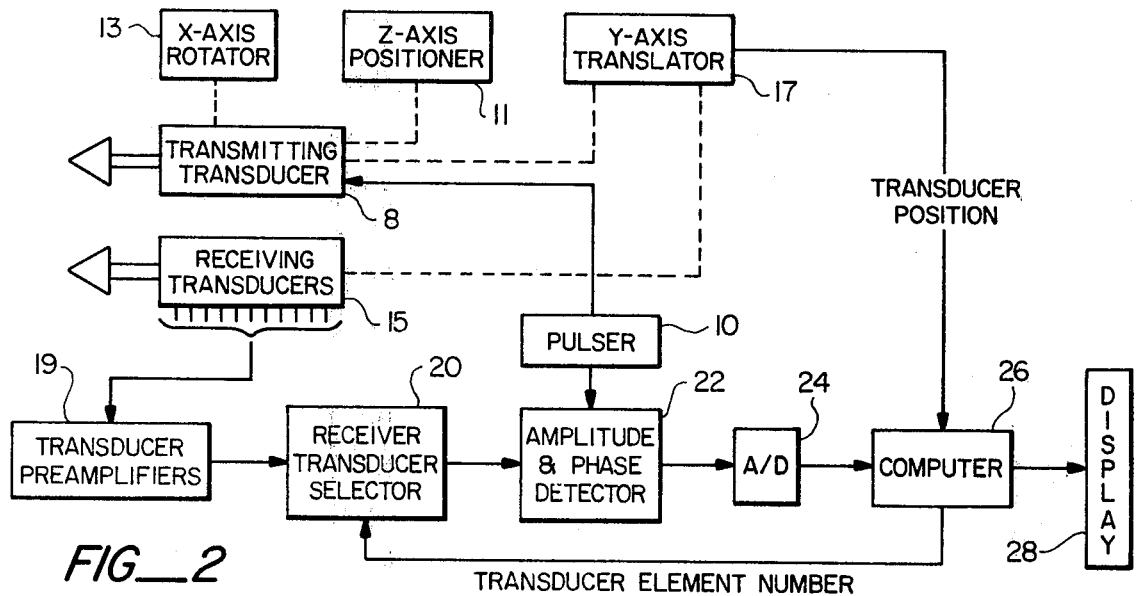
FIG__2
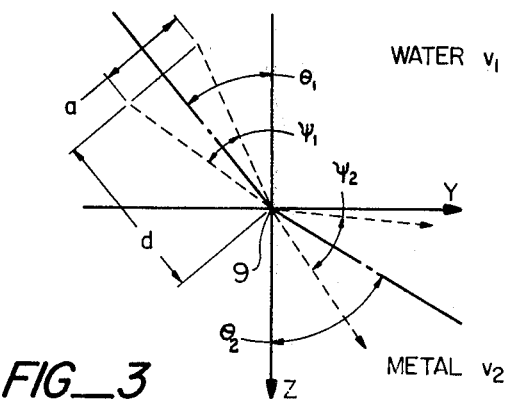
FIG__3
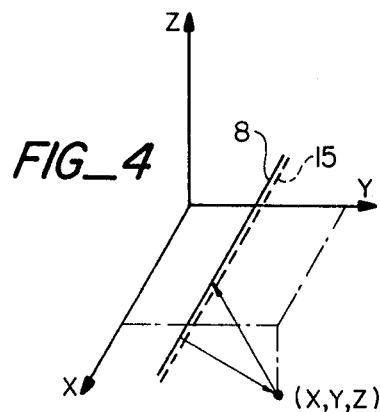
FIG__4

METHOD AND APPARATUS FOR ULTRASONIC IMAGING USING A LINE SOURCE AND A LINEAR RECEIVER ARRAY

The present invention generally relates to ultrasonic imaging and, more particularly, to transducer arrays and the signal processing circuits associated with such imaging.

Pulse-echo acoustic imaging has the problem of obtaining adequate resolution when collimated acoustic beams are used. An acoustic beam of approximately 1" in diameter is required to obtain satisfactory collimation for imaging; however, this diameter is too large for most practical imaging applications. Normally a beam having a smaller diameter is used and the corresponding decrease in resolution is accepted as a compromise. If, on the other hand, focused acoustic beams are used in pulse-echo imaging, then only a flaw located within the focal zone can be imaged. In addition, focused acoustic waves are extremely difficult to form and scan electronically.

Another technique for ultrasonically imaging objects of interest is acoustic holography. As presently practiced acoustic holography uses a single focused transducer that is positioned with respect to the object of interest so that acoustic waves are focused on its surface. The transducer operates as both the source and the receiver and a mechanical bridge is used to move the transducer from one position to another and to scan the object. The echo signal received by the transducer is converted into an electrical signal and then is mixed with a reference signal. The resulting signal is thereafter applied to a light source which exposes a portion of a photographic film corresponding to the position of the transducer with respect to the object. Others use a computer reconstruction scheme. During operation the mechanical bridge moves the transducer across the object so that object is scanned point by point and the photographic film is fully exposed. The film is later developed and an image is formed by illuminating the film with coherent light.

At the present time acoustic holographic imaging as described above requires so much time to perform that it is almost not commercially feasable. If the transducer makes 128 by 128 measurements, the scanning bridge must physically move the transducer over 16,000 times and in a typical system it takes over twenty minutes to record this much data. If an electrically scanned array of multiple transducers is used to increase the scanning speed, there is a difficulty in generating sufficient power from the tiny transducers to penetrate deeply into the object of interest. This is a special problem when large steel forgings are imaged because they have dimensions of 10 to 12 inches in thickness.

Another method for ultrasonic imaging is by backwave reconstruction. An acoustic wave is scattered from an object of interest and the phase and amplitude of the scattered wave front is detected and digitized. The image is then digitally calculated by employing angular spectrum diffraction theory. This process is described in an article entitled "Computer Reconstruction of Images From Ultrasonic Holograms" by Boyer et al., which appeared in Vol. 2 of (Acoustical Holography) (Metherell and Larmore, eds.), Plenum Press, New York, 1970, pp. 211-223. This method is also described in an article entitled "Digital Ultrasonic Wavefront Reconstruction in the Near Field" by David Van Rooy, (IBM Publication No. 320 2402) dated May 19, 1970.

An additional system for holographic imaging utilizes a cylindrical insonifying transducer and a linear receiver array located perpendicularly to its longitudinal axis. The insonifying transducer and the receiver array are translated along an axis parallel to the insonifying transducer so that the receiver array sweeps out a planar detection area. This system is described in an article entitled "A Holographic System for use in the Ocean" by Wade et al. published in Vol. 3 of (Acoustical Holography), (Metherell, ed.), Plenum Press, New York, 1971, pp. 225-245, and an article entitled "Experimental Results from an Underwater Acoustical Holographic System" by Wollman and Wade which was published in vol. 5 of (Acoustical Holography), (Green, ed.), Plenum Press, New York, 1971, pp. 159-174.

Although the above-described array solves the problem of generating sufficient power for acoustic holographic imaging, the array has a limited field of view. When the size of the object of interest is wider than ½ the length of the receiver array, the object of interest is not seen by the system. In this circumstance the acoustic waves are reflected by the object beyond the end of the array and the acoustic waves are not received by the array. This array also has the problem of compensating for an aspect ratio which changes with the position of the object of interest. For a point object the array provides an elliptical pattern and the aspect ratio is:

$$\frac{a}{b} = \sqrt{2} \frac{D}{\sqrt{D^2 + x_0^2}} \qquad \text{EQ. 1}$$

Where
  a=length of the minor axis
  b=length of the major axis
  D=depth to the object
  $X_o$=position of object relative to the center of the aperture.

One object of the present invention is to scan a specimen at high speed. This object is achieved by electronically scanning a linear array of receiver transducers placed parallel with a line source. The line source and the array of receiver transducers are mechanically translated step by step along a line perpendicular to the array, thus sweeping out an area. The line source is pulsed many times a second and each receiver is electronically sampled in turn in one fixed position. When all of the receivers have been sampled, the line source and the receiver array are indexed to a new position and the procedure is repeated until the entire detection area is scanned.

An additional object of the present invention is to obtain an image of the specimen at high speed. This object is achieved by using backwave reconstruction to obtain a digital image of the specimen. The signals detected by the receiver transducers are stored in a computer memory. The computer projects backwards the sound pattern detected by the receiver array using the wave equations and generates a digital image representing the shape of the specimen which originally scattered the acoustic waves detected by the receiver array. This calculation process occurs in a very short period of time because high speed data gathering and computing systems are readily available.

A further object of the present invention is to ultrasonically image specimens using relatively simple electronic circuits and inexpensive components. It is a feature of the present invention that the preferred embodiment can be constructed using commercially available equipment and operated with a readily obtainable software.

Another object of the present invention is to propagate sufficient acoustic energy so that flaws can be imaged in steel to a depth of 12". This object is achieved by the use of a large rectangular transmitting transducer that transmits acoustic waves to a line focus.

An additional object is to increase the field of view of an acoustic imaging system. This object is achieved by using a line source located parallel with an elongate array of receiver transducers. As long as the specimen is no wider than the length of the receiver array, the entire width of the specimen will reflect acoustic energy back to the receiver array. Thus, the present invention provides at least twice the field of view as the prior art system described above.

A further object of the present invention is to develop an apparatus that avoids having to correct for an aspect ratio that is a function of the position of the specimen. It is an advantage of the present invention that the aspect ratio can be corrected by simply distorting the dimensions of the data matrix in such a way that ellipses appear as circles. In the case of a point object, for example, the aspect ratio can be corrected by distorting the dimensions by the square root of two.

The above objects and advantages, along with others described herein, are achieved by an apparatus for ultrasonically imaging specimens or objects of interest comprising an elongate source of coherent acoustic waves adapted for transmitting coherent acoustic waves to a line focus. The apparatus further includes an elongate linear array of substantially point receivers located parallel to the elongate source and substantially at the line focus. The elongate source and the receiver array are translated relative to the specimen so that an area is swept out across the specimen and the specimen is imaged by the acoustic waves.

Additional objects and features of the invention will appear from the following description in which the preferred embodiments have been set forth in detail in conjunction with the accompanying drawings.

FIG. 1 is a diagrammatic perspective view of an elongate source of coherent acoustic waves focused to a line located on the surface of an object of interest and an elongate receiver array located parallel to the elongate source and substantially at the line focus.

FIG. 2 is a block diagram of the apparatus and signal processing circuit used in conjunction with the apparatus of FIG. 1.

FIGS. 3 and 4 are diagrams illustrating, with respect to coordinate systems, the paths of the acoustic waves developed by the apparatus of FIG. 1.

FIG. 1 illustrates a transmitting transducer and a receiver array according to the present invention. The apparatus as shown in FIG. 1 is used for imaging a flaw 5 located in a steel plate 6. The apparatus includes an elongate rectangular piezoelectric transmitting transducer 8. The transmitting transducer has a cylindrical transmitting surface for focusing the acoustic waves transmitted therefrom into a line focus 9. The transducer is commercially available and in the preferred embodiment can be fabricated from three 2"×1" rectangular pieces of PZT to form a 6" long by 1" wide transducer element. The transducer is energized by a pulser 10 of known construction and operates at a frequency in excess of 1 megahertz. The transducer is positioned so that the line focus 9 is coincident with the surface of the material 6 being imaged.

The acoustic waves transmitted by the transducer 8, FIG. 1 are coupled into the plate 6 by a hollow wedge (not shown) that is filled with water. The bottom edge of the wedge has a thin acoustic-wave-transparent membrane. In addition, a thin film of water is maintained between the membrane and the plate 6 in order to complete the coupling of acoustic waves into the object of interest. The hollow wedge and the film of water are not shown in FIG. 1 because of clarity and because they are of conventional construction.

The transmitting transducer 8, FIG. 1 is mounted so that it can be rotated in a cylindrical path about the line focus 9. In FIG. 3 this motion of the transmitting transducer about the axis 9 is illustrated by the angle $\Theta_1$. In FIG. 2 the apparatus which permits this cylindrical rotation is the X-axis rotator 13. This rotator is a mechanical stage of conventional construction and enables the diverging acoustic waves propagating from the transmitting transducer to be steered inside of plate 6. The X-axis rotator permits the waves reflected by the flaw 5 to be maximized and also permits the exclusive use of shear waves for acoustic imaging. The exclusive propagation of shear waves in the plate is achievable because the transmitting transducer 8 can be tilted about the X-axis to a position beyond the critical angle for propagating longitudinal acoustic waves in steel. At this position only mode-converted shear waves can propagate in the plate.

It should be understood that the transmitting transducer 8, FIG. 1 can also be characterized as a line source of acoustic waves. Another suitable line source transducer can be fabricated by using an elongate rectangular piezoelectric transducer with a flat transmitting surface which is bonded to a cylindrical acoustic lens. The acoustic waves are propagated from it to a line focus located substantially at the surface of the object being imaged. In addition, a linear line source containing a piezoelectric element that is equal in all dimensions to that of the receiver array described below can also be used. This array may or may not be segmented and the acoustic radiation pattern produced therefrom is controlled by the element length and width while the frequency is controlled by its thickness. For small transducer element widths the acoustic radiation pattern is approximately the same as that formed by the focused line source described above and is likewise focused on the surface of the object of interest. A further suitable line source transducer is a cylindrically shaped piezoelectric transducer having a length and wall thickness equivalent to the focused transducer 8, FIG. 1 described above. The radius of curvature of the cylindrical transducer should be as small as possible in order to replicate the acoustic wave field pattern of an ideal line source.

The transmitting transducer 8, FIG. 1 is mounted so that it can be translated with respect to the plate 6 and the line focus 9 continuously positioned on the surface of the plate. In FIG. 2 this translation apparatus is identified as the Z-axis positioner 11. The transmitting transducer is also connected to a Y-axis translator 17, FIG. 1 which moves the transmitting transducer and the receiver array simultaneously across the surface of the plate so that the line focus sweeps out an area across the plate. The Z-axis positioner and the Y-axis translator are both mechanical stages and are similar to the X-axis rotator.

FIG. 3 is a side elevational view of the coordinate system of the apparatus of FIG. 1 and illustrates the propagation of acoustic waves by the apparatus. It can be seen from FIG. 3 that when the transmitting transducer 8 is rotated about the X-axis by an angle $\Theta_1$, the beam of acoustic waves in the steel plate 6 is correspondingly rotated by $$\theta_2 = \sin^{-1}\left\{ \frac{v_2}{v_1} \sin \theta_1 \right\} \quad \text{EQ. 2}$$

where $v_1$ = velocity of sound in water
$v_2$ = velocity of sound in the material.

The velocity of sound ($v_2$) in the plate 6 has two values, one for the propagation of longitudinal acoustic waves and the other for shear waves. Depending on the angle shear waves are generated along with longitudinal waves but shear waves travel at roughly one half of the velocity of the corresponding longitudinal waves.

As discussed above the transmitting transducer 8, FIG. 1 can be rotated about the X-axis sufficiently so that only shear waves propagate in the plate 6. The angle of incidence $\Theta_1$ for which longitudinal waves no longer exist in the plate is found by the formula $$\theta_{2l} = \sin^{-1}\left\{ \frac{v_{2l}}{v_1} \sin \theta_1 \right\} = 90° \quad \text{EQ. 3}$$

where the subscript l indicates longitudinal waves or $$\sin \Theta_1 = v_1/v_{2l} \quad \text{EQ. 4}$$

The corresponding angle for the propagation of shear waves in the plate is $$\theta_{2s} = \sin^{-1}\left\{ \frac{v_{2s}}{v_1} \sin \theta_1 \right\} \quad \text{EQ. 5}$$

or $$\theta_1 = \sin^{-1}\left\{ \frac{v_{2s}}{v_{2l}} \right\}$$

The angular spread of the wedge of these waves depends on the ratio of the focal length of the transducer to the width of the transducer. Referring to FIG. 3 the distance between the transducer and the line focus 9 is identified as distance d and the width of the transducer is identified by the letter a. This ratio is called the F number where F=d/a. It can also be seen from FIG. 3 that the wedge angle for the acoustic waves in water is given by $$\psi_1 = 2 \tan^{-1}\left( \frac{1}{2F_1} \right) \quad \text{EQ. 6}$$

When the acoustic waves pass from the water into the steel plate 6, the velocity of the acoustic waves increases ($v_2$ is larger than $v_1$) and the wedge angle in the plate correspondingly increases to $$\psi_2 = 2 \tan^{-1}\left( \frac{1}{2F_2} \right) = 2 \sin^{-1}\left\{ \frac{v_2}{v_1} \sin(\psi_1/2) \right\} \quad \text{EQ. 7}$$

Equation 7 can be manipulated to yield the result $$F_2 \cong \frac{v_1}{v_2} F_1 \quad \text{EQ. 8}$$

In some circumstances it is desirable to propagate the acoustic waves orthogonally with respect to the surface of the plate and directly into it. In this case the transducer is not rotated about the X-axis and $\Theta_1$ is zero. This mode of operation is called the zero beam and results in more longitudinal waves being propagated in the plate than in any other mode.

It should be understood from the foregoing that the sound field propagated in an object of interest can be manipulated and controlled in a plurality of ways by the present invention. The width of the transducer a, the focal length d, the angle of incidence $\Theta_1$, and the acoustic velocity of the coupling medium can all be varied to suit differing circumstances.

One of the advantages of this flexibility is that different objects of interest can be imaged using shear waves exclusively. The transmitting transducer can be rotated about the X-axis past the critical angle so that longitudinal waves are no longer propagated within the object of interest. One of the features of this mode of imaging is that all of the erroneous reflections from the back surface of the object of interest are eliminated because no energy strikes the back surface of the object of interest directly below the transmitting transducer. In other modes these reflections frequently intermingle with the waves reflected from flaws and cause erroneous images.

Referring to FIG. 1 the apparatus also includes a linear array of substantially point receiver transducers 15. These receiver transducers are positioned as close to the line focus 9 as possible and are in parallel with the longitudinal axis of the transmitting transducer 8 as well as the line focus 9. In other words, the receiver array has an axis of maximum sensitivity which is located substantially coincident with the line focus 9. These axes are illustrated in FIG. 4 although displaced slightly for clarity. The receiver array is fabricated from conventional piezoelectric materials such as PZT. It is desirable to have the receiving elements fabricated as small as possible in order that each will accept acoustic energy over a wide angle of incidence. It is believed that receiving elements for the preferred embodiment operate satisfactorally if each has a width and length less than ¼ the wave length of the acoustic waves propagated in the object of interest.

The transmitting transducer 8 and the array of receiving elements 15 are mounted together for simultaneous translation across the surface of the object of interest. This translation is performed by the Y-axis translator 17, FIG. 2 described above and in the preferred embodiment is in a direction parallel to the Y-axis. The Y-axis translator moves the transmitting transducer and the receiver array together across the object of interest so that the line focus 9 and the axis of maximum sensitivity of the receiver array sweep out an area across the surface of the object of interest and a detection plane is formed that is coincident with this swept area.

Referring to FIG. 2, each receiver element detects the acoustic waves incident thereon, and converts these waves to electrical signals which are amplified by the preamplifiers 19. Each receiver element 15 is connected to an individual preamplifier. The amplified signals are then passed to a receiver transducer selector 20 which is a semiconductor switch that selectively samples the output signals from the receiver elements. The switching between the receiver elements is controlled by a digital computer 26 that commands the selector to select a predetermined transducer element. The amplified transducer output signal selected by the selector is passed to an amplitude and phase detector 22. The detector also receives a timing pulse from the pulser 10 so that the phase shift between the propagated acoustic waves and the detected acoustic waves can be measured. The amplitude and phase detector is of known construction and has an output representing the real and imaginary (or the amplitude and phase) components of the complex echo signal received on the detection plane by the receiver array. This data from the detector is digitized by an analog to digital convertor (A/D) 24 and is stored in the memory of the computer 26.

The computer 26, FIG. 2 is a PDP 11/34 computer manufactured by Digital Equipment Corporation of Maynard, Mass. In the preferred embodiment the computer has a storage capacity of 48 K bytes and operates with the following programs:

Digital Equipment Corporation's RSX 11 M Operating System;

Battelle's FORTRAN—Coded Ultrasonic Imaging Software Package.

To scan an object of interest, which in FIG. 1 is the steel plate 6, the transmitting transducer 8 and the receiver array 15 are positioned as shown in FIG. 1. The transmitting transducer is located so that its line focus 9 is coincident with the surface of the plate and the axis of maximum sensitivity of the receiver array is positioned so that it is parallel to the line focus and as close to it as possible. This positioning is illustrated in FIG. 4. During operation the transmitting transducer is pulsed many times per second by the pulser 10 and each pulse has a frequency in excess of 1 megahertz. The pulse also sends a timing signal corresponding to each pulse to the amplitude and phase detector 22 that is used for the phase shift measurement.

While the transmitting transducer is being pulsed, the computer 26 commands the receive transducer selector 20 to sample each receiving element in turn along the array 15 so that the array is scanned. The complex echo signal received by each element is amplified and passed to the amplitude and phase detector 22. The amplitude and phase detector measures the amplitude of the detected signals and the phase shift between transmitted and detected signals. The output of the amplitude and phase detector is digitized and stored in the memory of the computer at a location corresponding to the position of the transducer element which detected the signal.

After all of the receiver elements 15, FIG. 1 have been sampled, the transmitting transducer 8 and the receiver array 15 are indexed by the Y-axis translator 17 to a new position on the object of interest. The above-described scanning procedure is repeated and then the transmitting transducer and the receiver array are indexed again. This entire procedure is repeated over and over until the scanning area has been completely scanned and the computer memory contains an array of complex numbers representing the acoustic waves scattered from the flaw 5 and detected by the receiver elements in the detection plane.

After the computer memory has been filled with an array of complex numbers representing the sound scattered from the flaw 5, the computer 26 is used to predict the shape of the flaw and to generate a digital image of it. The computer is able to perform this calcualtion because the acoustic waves scattered by the flaw assume a unique distribution on the detection plane. The unique distribution occurs because the propagation of sound in the plate always obeys the wave equation $$(\nabla^2 + k^2) f(x,y,z) = 0 \qquad \text{EQ. 8}$$

Where
$\nabla$ = divergence operator
$k$ = wave number
$f(x,y,z)$ = measured values of the wave on the plane.

The computer 26, FIG. 1 takes the sound pattern measured on the detection plane and projects that pattern backwards in space as predicted by the wave equation to obtain a digital image of the flaw 5. The image is calculated according to angular spectrum diffraction theory. Under this theory the angular spectrum of plane waves on any plane Z is found by multiplying the angular spectrum of plane waves incident on the detection plane Z=0 by an exponential factor which accounts for the phase change due to the distance propagated. In effect, the wave front is mathematically propagated backwards in space so that the resulting intensity of the flaw which originally scattered the waves is determined.

The calculation begins with the computer 26, FIG. 2 having four channels of information for each signal measurement. These channels are the phase and amplitude of the detected signal and the x and y position on the detection plane of the receiver element which detected the signal. The x and y position of the receiver elements is obtained from the Y-axis translator 17 and the transducer element number which was sent to the transducer scanner 20. This data represents the complex value of the field $f(x,y,z)$, on the detection plane $z=0$. That is to say $f(x,y)$ is measured.

From this data the computer next takes the two dimensional Fourier transform of $f(x,y,0)$ to obtain a spectrum of plane waves $F(u, v, 0)$.

After taking the Fourier Transform of the field on the detection plane, the computer multiplies the spectrum of plane waves by the backward propagation factor $$\exp\left[-jkz \sqrt{1 - \alpha^2 - \beta^2}\right] \qquad \text{EQ. 9}$$

Where $\alpha = \dfrac{2\pi u}{k}$ and $\beta = \dfrac{2\pi v}{k}$.

This term incorporates the wave equation which is equation 8 above. This term permits the angular spectrum of plane waves to be calculated on a predetermined image plane $z=z$.

To locate the flaw 5, FIG. 1 in the plate 6, the calculation is repeated over and over for increasingly larger values of z until a bright spot appears on the display 28. This is the flaw. Different values of z are then used around this value of z which caused the spot to appear until the optimum image plane is found. The optimum image plane is typically the plane in which the edges of the flaw appear at their sharpest.

Once the optimum image plane is found, the inverse Fourier transform of $$F(\frac{\alpha}{\lambda}, \frac{\beta}{\lambda}, z) \quad \text{EQ. 10}$$

is taken. This process results in a digital representation of the image with a complex amplitude of f(x,y,z).

When the image plane z=z coincides with the plane of the flaw, the result is an image of the flaw in focus.

The computer 26, FIG. 2 next plots the magnitude, $$|f(x,y,z)|^2, \quad \text{EQ. 11}$$

and/or the phase $$\Theta(x,y,z). \quad \text{EQ. 12}$$

After this computation process has been completed, then either the intensity or the phase of the image is displayed on an imaging raster scan television screen 28, such as the I-1000 which is commercially available from De Anza Corporation.

In one embodiment of the present invention which was actually constructed, a linear array of 128 receiver elements was used. The transmitting transducer had a dimension of 1" by 6". It has been calculated that if a flaw were located approximately 12.5 cm in steel, then the 128 receiver elements could be scanned in approximately 100 microseconds. If 128 lines of data are taken along the y-axis, the total data gathering time should be as short as 12.8 milliseconds. The detection plane then is a 128 by 128 data set which is stored in the computer memory. The De Anza raster scan television screen permitted the display of individual pixels with varying intensities on a 256×256 grid. With a PDP 11/70 computer having a memory of 256 K bytes and operating at a speed of 900 ns. per word the reconstruction time for a 128 by 128 data set was approximately 30 seconds and a digital image of the flaw was obtained in less than one minute.

Although the best mode contemplated for carrying out the present invention has been herein shown and described, it should be apparent that modification and variation may be made without departing from what is considered to be the subject matter of the present invention.

What is claimed is:

1. Apparatus for ultrasonically imaging objects of interest, comprising:
   (a) an elongate source of coherent acoustic waves adapted for transmitting coherent acoustic waves to a line focus;
   (b) an elongate linear array of substantially point receivers, said receiver array being located parallel to said elongate source and substantially at the line focus so that the acoustic waves propagated from the source interact with an object of interest and are detected by the receiver array; and
   (c) means connected to said elongate source and receiver array for translating both said source and array relative to the object of interest so that an area is swept out across the object of interest and said object is imaged.

2. An apparatus as in claim 1 including means connected to the elongate source for positioning said source during translation so that the line focus is substantially coincident with the surface of the object being imaged.

3. An apparatus as in claim 1 including means connected to the elongate source for rotating said source about the line focus thereby controlling the propagation of both the longitudinal and the mode-converted shear waves in the object of interest.

4. An apparatus as in claim 1 including switch means connected to the receivers for individually sampling the receivers for signals detected by the receivers and wherein the translating means moves the source and the receiver array in a step-by-step manner, said switch means being adapted for sampling all of the receivers in the array between each translation of the apparatus.

5. Apparatus for ultrasonically imaging objects of interest, comprising:
   (a) an elongate source of coherent acoustic waves adapted for transmitting coherent acoustic waves to a line focus;
   (b) an elongate linear array of substantially point receivers having an axis of maximum sensitivity, said axis of maximum sensitivity being located substantially coincident with the line focus so that the acoustic waves propagated from the source interact with an object of interest and are detected by the receiver array; and
   (c) means connected to said elongate source and receiver array for simultaneously translating both said source and array relative to the object of interest so that the line focus and the axis of maximum sensitivity sweep out an area across the surface of the object of interest and said object is ultrasonically imaged.

6. Apparatus for ultrasonically imaging objects of interest, comprising:
   (a) a source of coherent acoustic waves adapted for transmitting and focusing coherent acoustic waves into an object of interest;
   (b) a linear array of substantially point receivers, said receiver array being located substantially at the focus of the focused acoustic waves so that the acoustic waves propagated from the source are scattered by the object of interest and are detected by the receiver array;
   (c) means connected to the source and the receiver array for translating both said source and array relative to the object of interest so that a detection plane is swept out across the object of interest; and
   (d) means connected to the receiver array for computing a digital representation of the object which scattered the acoustic waves detected by the receiver array.

7. An apparatus as in claim 6 wherein said computing means calculates a digital representation of the pattern of acoustic waves scattered by the object of interest that are incident on the detection plane.

8. An apparatus as in claim 6 wherein said computing means calculates a digital representation of the pattern of acoustic waves scattered by the object of interest that are incident on a plane containing the object of interest by back projecting a digital representation of the pattern of acoustic waves incident on the detection plane.

9. Apparatus for ultrasonically imaging objects of interest, comprising:
   (a) an elongate source of coherent acoustic waves adapted for transmitting coherent acoustic waves to a line focus;
   (b) an elongate linear array of substantially point receivers, said receiver array being located parallel to said elongate source and substantially at the line focus so that the acoustic waves propagated from the source are scattered by the object of interest and are detected by the receiver array;

(c) means connected to the source and the receiver array for translating both said source and array relative to the object of interest so that a detection plane is swept out across the object of interest; and (d) means connected to the receiver array for computing a digital representation of the object which scattered the acoustic waves detected by the receiver array, said computing means backprojects a digital representation of the pattern of acoustic waves incident on the detection plane to a second plane by multiplying said digital representation by an exponential factor which is a function of the change in phase of the acoustic waves due to the distance traveled by said waves from the detection plane to the second plane.

10. An apparatus as in claim 9 including means connected to the computing means for displaying the digital representation of the image of the object of interest.

11. Method for ultrasonically imaging objects of interest, comprising the steps of:

(a) Transmitting a coherent acoustic wave to a line focus using an elongate array;

(b) scattering the focused acoustic wave off an object of interest;

(c) detecting the scattered acoustic wave with an elongate array of receivers, each receiver of said array of receivers being sampled in turn to scan across said line focus;

(d) translating said two arrays relative to the object of interest so that a detection plane is swept out across the object;

(e) repeating steps (a) through (d) as said two arrays are translated; and (f) computing a digital representation of the object which scattered the acoustic waves detected by the receiver array.

12. A method as in claim 11 including the step of calculating a digital representation of the pattern of acoustic waves scattered by the object of interest that are incident on a plane containing the object of interest by back projecting a digital representation of the pattern of acoustic waves incident on the detection plane.

13. A method as in claim 11 including the step of back projecting a digital representation of the pattern of acoustic waves incident on the detection plane to a second plane by multiplying said digital representation by an exponential factor which is a function of the change in phase of the acoustic waves due to the distance traveled by said waves from the detection plane to the second plane.

14. A method as in claim 11 including the step of displaying the digital representation of the image of the object of interest.

* * * * *